(12) United States Patent
Zhang et al.

(10) Patent No.: US 10,969,262 B1
(45) Date of Patent: Apr. 6, 2021

(54) FILTERING CONTAINER WITH TIME-BASED CAPACITIVE FLOW MONITORING

(71) Applicant: LARQ, Inc., Foster City, CA (US)

(72) Inventors: Li Zhang, Foster City, CA (US); Josh Abell, Foster City, CA (US); Doug Collins, Foster City, CA (US)

(73) Assignee: LARQ, INC., Foster City, CA (US)

( * ) Notice: Subject to any disclaimer, the term of this patent is extended or adjusted under 35 U.S.C. 154(b) by 0 days.

(21) Appl. No.: 16/996,818

(22) Filed: Aug. 18, 2020

(51) Int. Cl.
*G01F 9/00* (2006.01)
*G01F 23/26* (2006.01)
(Continued)

(52) U.S. Cl.
CPC ............... *G01F 9/005* (2013.01); *A61L 2/10* (2013.01); *A61L 2/24* (2013.01); *C02F 1/003* (2013.01); *C02F 1/325* (2013.01); *G01F 23/265* (2013.01); *G01F 23/268* (2013.01); *G01N 15/0826* (2013.01); *A61L 2202/11* (2013.01); *A61L 2202/14* (2013.01); *C02F 2201/326* (2013.01); *C02F 2209/40* (2013.01); *C02F 2209/42* (2013.01); *C02F 2209/445* (2013.01); *C02F 2303/04* (2013.01); *C02F 2303/16* (2013.01);
(Continued)

(58) Field of Classification Search
CPC ........ G01F 13/06; G01F 23/268; G01F 9/005; G01F 23/265; C02F 1/003; C02F 2209/42; C02F 1/325; C02F 2201/326; C02F 2209/40; C02F 2209/445; C02F 2303/04; C02F 2303/16; C02F 2307/04; A61L 2/10; A61L 2/24; A61L 2202/11; A61L 2202/14; G01N 2015/084; G01N 15/0826
See application file for complete search history.

(56) References Cited

U.S. PATENT DOCUMENTS 7,107,838 B2    9/2006  Chai et al.
7,487,677 B2    2/2009  Chai et al.
(Continued)

FOREIGN PATENT DOCUMENTS

CN    100574842    12/2009
CN    101795976    2/2013
(Continued)

*Primary Examiner* — Terry K Ceceil
(74) *Attorney, Agent, or Firm* — ARC IP Law, PC; Joseph J. Mayo

(57) ABSTRACT

A container for liquids that measures flow using capacitive sensor strips. Capacitance data is processed to identify points in time when liquid levels reach or pass specified levels, and flow metrics may be calculated from these points in time. Embodiments may use one or more horizontal capacitive strips, which may be located in a removable sensing package that is not in contact with the liquid in the container. Because discrete points in time are used instead of analog fluid level measurements, flow metrics are more robust than previous approaches that use vertical parallel capacitors within the container to continuously measure fluid levels. The container may have a filter, and capacitance data may be used to calculate metrics such as filter flow rate and cumulative volume through the filter, and to identify when the filter needs to be replaced. Embodiments may use UV light to sanitize the liquid or the filter.

25 Claims, 16 Drawing Sheets

(51) Int. Cl.
    *C02F 1/00*     (2006.01)
    *C02F 1/32*     (2006.01)
    *A61L 2/10*     (2006.01)
    *A61L 2/24*     (2006.01)
    *G01N 15/08*     (2006.01)
    *G01F 13/00*     (2006.01)

(52) U.S. Cl.
    CPC ........ *C02F 2307/04* (2013.01); *G01F 13/006* (2013.01); *G01N 2015/084* (2013.01)

(56) References Cited

U.S. PATENT DOCUMENTS

| | | | |
|---|---|---|---|
| 7,666,288 B2 | 2/2010 | Sato | |
| 7,905,144 B2 * | 3/2011 | Thobe | G01F 13/00 73/304 R |
| 8,171,802 B2 * | 5/2012 | Henderson | G01F 1/007 73/861.12 |
| 10,593,732 B2 | 3/2020 | Choi et al. | |
| 2010/0187168 A1 | 7/2010 | Moretto | |

FOREIGN PATENT DOCUMENTS

| | | |
|---|---|---|
| CN | 206809883 | 12/2017 |
| CN | 207085689 | 3/2018 |
| CN | 109665639 | 4/2019 |
| WO | 2015/197725 A1 | 12/2015 |

\* cited by examiner

FIG. 10
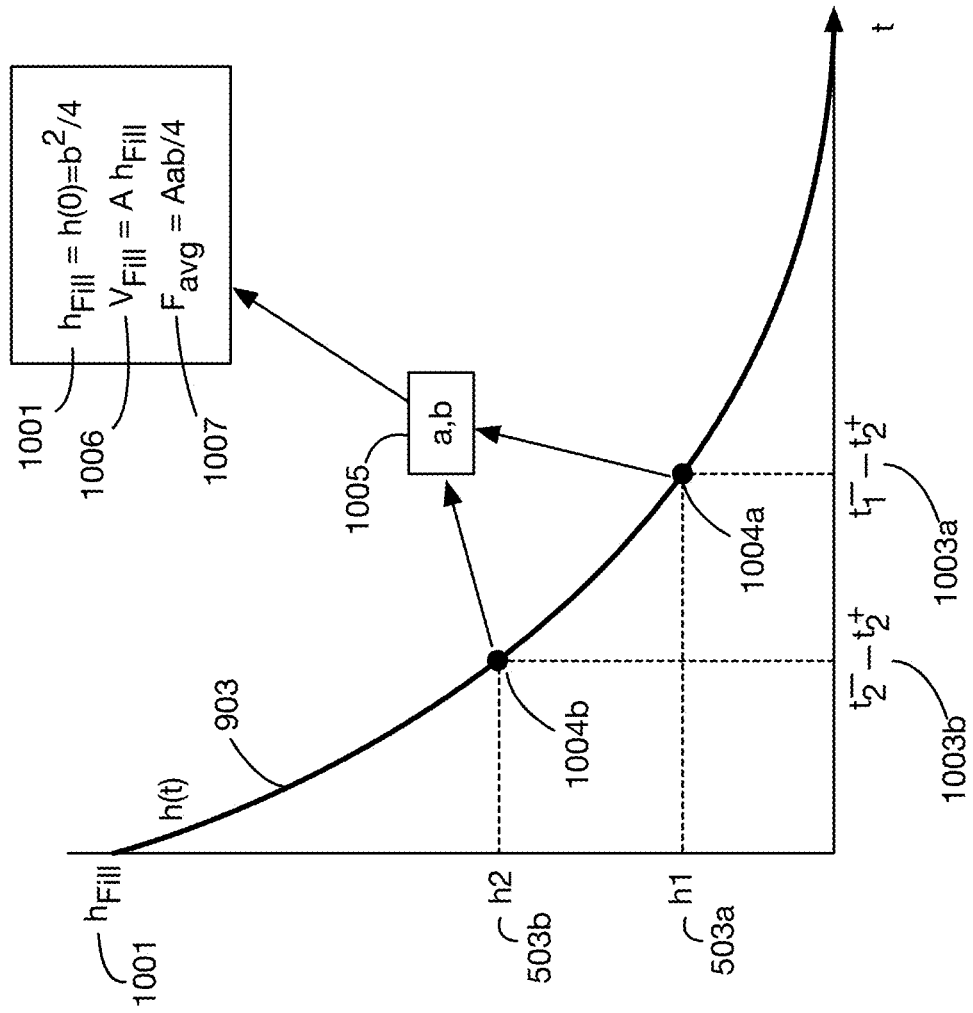
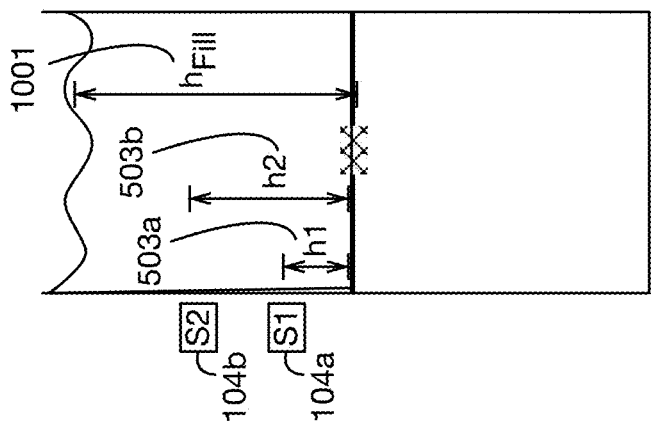

FILTERING CONTAINER WITH TIME-BASED CAPACITIVE FLOW MONITORING

BACKGROUND OF THE INVENTION

Field of the Invention

One or more embodiments of the invention are related to the fields of flow monitoring sensors and liquid filtering and sanitizing devices. More particularly, but not by way of limitation, one or more embodiments of the invention enable a filtering container with time-based capacitive flow monitoring.

Description of the Related Art

Filtering containers for water or other liquids are commonly used. For example, some water pitchers may include a built-in filter that can filter regular water. The pitcher may include a hopper to collect the regular water that is poured into the pitcher. The regular water flows through a filter at the bottom of the hopper and into the pitcher reservoir. The filtered water can then be poured out of the pitcher reservoir for consumption.

After a certain amount of water flows through the filter, the filter may get dirty or clogged with impurities and/or no longer remove impurities with sufficient efficacy. To maintain the full benefits of the filter, the filter should be periodically replaced with a new filter. In that regard, both consumers and filter companies like to be notified when the filter should be replaced. To provide such notice, electronics can be incorporated into the pitchers. However, many existing pitchers simply provide a notification to change the filter after a predetermined amount of time, regardless of the amount of water flow and regardless of the filter condition. Other pitchers with sensors may simply detect the number of times a lid to the pitcher is opened, and this method presumes that the user properly fully fills the pitcher each time the lid is opened.

To provide more accurate notifications that a filter should be changed, a filtering container may monitor the actual amount of liquid that flows through the filter. Some filtering containers known in the art use water level sensors integrated into the container. Typically, sensors used for water level sensing include a geometry of vertical sensor strips that often span from the top of the pitcher to the bottom of the pitcher. These strips may sense the level of water in a pitcher by measuring the capacitance between the two vertical sensor strips. The capacitance is dependent on the material surrounding the strips. In an empty container, air is surrounding the strips. In a full container, water is adjacent to the strips. In a partially full container, the capacitance is proportional to the height of the portion of the sensor that is adjacent to the water. Because water has a larger dielectric constant than air, the higher water level results in a larger measured capacitance. Therefore, as the water level increases, the capacitance also increases.

Existing capacitive sensor strips known in the art have several potential disadvantages. First, vertical sensor strips are often located on the inside surface of the pitcher so that the water directly contacts the strips. Although this improves the signal magnitude, such contact between the water and the vertical sensor strips may cause contamination of the water and may alter the taste of the water. Moreover, the vertical sensor strips may degrade, in response to being contacted by the water, and may then contaminate the water. Having the sensors inside the hopper may also require housing the readout electronics inside the hopper or providing electrical feedthroughs to connect the sensors in the hopper to any electronics housed outside of the hopper, both of which add significant points of failure to the system.

Second, because capacitance measurements can be sensitive to small changes in the relative position and geometry of the sensors, using vertical sensor strips to measure the water level typically requires careful calibration of absolute capacitance magnitude against water volume. Third, the measurements will be sensitive to any changes (or drift) in the baseline signal or environmental noise which will create an error in the measured volume. Finally, the use of dual vertical sensor strips pulls the area of maximum sensitivity towards the electrodes, thereby reducing the effectiveness of remote sensing (i.e., sensor strips that are not in contact with the water).

Despite these potential disadvantages of vertical sensor strips, in some applications it is important to continuously monitor the precise level of liquid in a container. This continuous level monitoring may be important for example in applications like gas tanks, or mil vats used by dairy farmers. However, for determining when a filter in a water pitcher should be replaced, it is not important to know the absolute water level in the hopper or pitcher at every moment but rather how much water has passed through the water filter over its lifetime and the flow rate of water through the filter. A vertical sensor strip system may be unnecessary for this purpose. A simpler system that monitors capacitance changes at specific points in time may be sufficient to monitor the flow and volume through a filter.

For at least the limitations described above there is a need for a filtering container with time-based capacitive flow monitoring.

BRIEF SUMMARY OF THE INVENTION

One or more embodiments described in the specification are related to a filtering container with time-based capacitive flow monitoring. One or more embodiments may monitor the flow of liquid into and through the container using capacitive sensors, by identifying specific points in time when capacitance data indicates that liquid levels reach or transition past specific levels in the container.

One or more embodiments may include a hopper that receives a liquid, with an inside wall that contacts the liquid and an outside wall that does not contact the liquid. A filter may be coupled to the hopper, and it may remove one or more substances from the liquid as it passes through the filter into a reservoir that stores the filtered liquid. One or more horizontal capacitive sensor strips may be proximal to the hopper. These strips may be located so that they are not in contact with the inside wall of the hopper or with the liquid. In one or more embodiments these strips may not extend vertically across the full height of the liquid in the hopper when the hopper is full.

A processor may receive and process capacitance data from the sensor strips. It may identify points in time in the capacitance data, where each point in time corresponds to an associated height of the liquid in the hopper. It may calculate one or more flow metrics from these points in time.

Although capacitive sensor strips may be of any size and shape, in one or more embodiments each strip may have a horizontal length that is greater than its vertical width.

In one or more embodiments, capacitance data received from the sensor strips may be the self-capacitance of each strip.

In one or more embodiments, the processor may analyze the capacitance data or the flow metrics over a time period to determine when the filter needs to be replaced.

An illustrative flow metric may be for example the flow rate through the filter. In one or more embodiments, this flow rate may be calculated by identifying two points in time in the time series of capacitance data, each corresponding to a height of liquid in the hopper. The flow rate may be calculated based on the time difference between these two points in time, and on the volume difference of the liquid in the hopper between the two corresponding liquid heights. The liquid heights may correspond to the height of two different sensor strips in the hopper, and the points in time may be times when the capacitance of each associated sensor strip is decreasing. Alternatively the two heights may correspond to a top and bottom edge of a single sensor strip, and the points in time may be based on when the capacitance of that single strip begins decreasing, and then stops decreasing.

Changes in flow rate over time may be used to determine when the filter is clogged or needs to be replaced.

In one or more embodiments, the flow rate calculation may be based on a flow rate model, which may be for example either a constant flow rate model or a variable flow rate model. A variable flow rate model may for example assume that the flow rate varies with the height of the liquid in the hopper.

Another illustrative flow metric may be for example the liquid volume added to the hopper when it is filled. This volume may be calculated based on a filter flow rate, possibly using a flow rate model that may be constant or variable, and on a time difference between a time when capacitance of one of the sensor strips is increasing (during filling, for example), and when it is decreasing (during filtering, for example). One or more embodiments may track the total amount of liquid added to a hopper over a time period to determine when the filter needs to be replaced.

In one or more embodiments the horizontal capacitive sensor strips may be in a sensing package that can be attached to or detached from the outside wall of the hopper. The strips may be inside a housing of the sensing package. In one or more embodiments the outside wall of the hopper may mate with the sensing package when it is attached to the hopper.

In one or more embodiments, the processor may transmit a message or a command based on the capacitance data. For example, it may activate an ultraviolet light that may direct ultraviolet radiation toward one or more of the hopper, the filter, the reservoir, the liquid, and the filtered liquid.

One or more embodiments may include or interface with additional sensors, such as a motion sensor for example. The processor may analyze motion sensor data to determine whether changes in capacitance data are due to motion of the container.

BRIEF DESCRIPTION OF THE DRAWINGS

The above and other aspects, features and advantages of the invention will be more apparent from the following more particular description thereof, presented in conjunction with the following drawings wherein:

FIG. 10 shows an illustrative calculation of the volume of liquid added to the hopper of a container using the flow rate model of FIG. 9.

DETAILED DESCRIPTION OF THE INVENTION

A filtering container with time-based capacitive flow monitoring will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
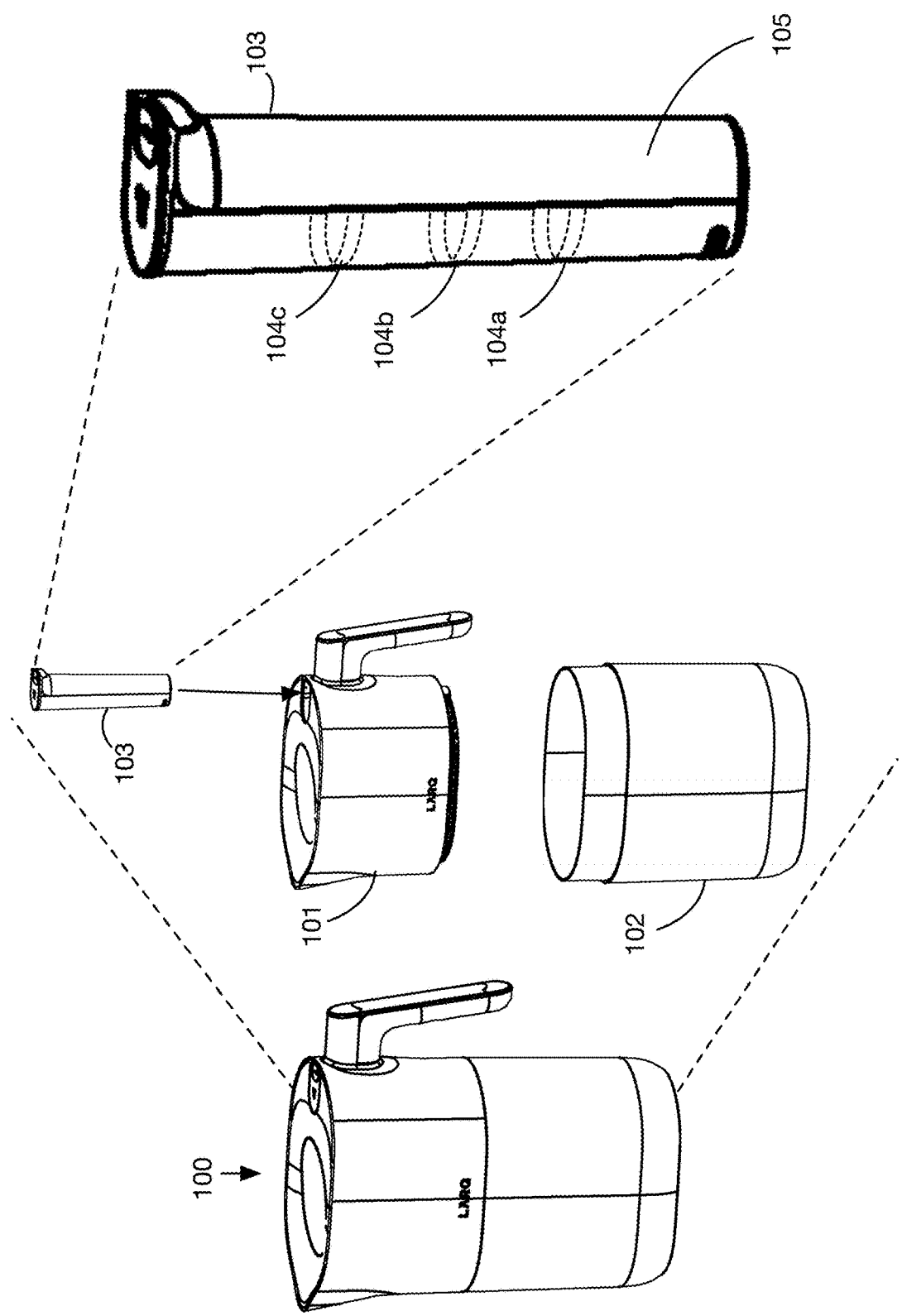
FIG. 1 shows an illustrative container with a filter, which includes an electronics module containing horizontal capacitive strips that are used to sense flow of liquid through the filter.

FIG. 1 shows an illustrative filtering container 100, and an exploded view of container 100 which includes a hopper 101 into which a liquid is poured, and a reservoir 102 that receives filtered liquid exiting the hopper 101. A filter or filters of any type may be placed between hopper 101 and reservoir 102 (or it may be integrated into either or both of the hopper or the reservoir); the filter may remove one or more impurities from the liquid as it passes from the hopper to the reservoir. For example, without limitation, the container 100 may be a portable water pitcher with an integrated filter.

Container 100 may also contain a sensing package 103 that may include sensors or other electronics. In the embodiment shown in FIG. 1, sensing package 103 is a "wand"-shaped component that can attach to hopper 101 by sliding into a corresponding indentation in the hopper; the wand can be removed for example for cleaning of the container, so that the electronic components in the wand are not exposed to hot water or steam during cleaning. In one or more embodiments, the sensing package may be integrated into the hopper 101 directly. Sensing package 103 may have various electronic components enclosed in a housing. In one or more embodiments, the housing of sensing package 103 may be constructed of a plastic material such as for example Tritan™ plastic, SMMA (styrene methyl methacrylate), SAN (styrene acrylonitrile resin), or PC (polycarbonate). FIG. 1 shows a close-up view of an embodiment of sensing package 103. Within a plastic enclosure 105, sensing package 103 contains three capacitive sensor strips 104a, 104b, and 104c. These strips may be used in one or more embodiments to measure flow of liquid into and out of hopper 101, as described below. These strips detect liquid via its effect on capacitance; since the dielectric constant of water for example is much higher than that of air, a capacitive strip in the proximity of water will have a higher capacitance than one near an empty part of a hopper. One or more embodiments may contain any number of capacitive sensor strips, including but not limited to the three strips shown in FIG. 1. The sensor strips may be of any size, shape, spacing, and orientation. They may be made of any material, including for example copper or other metals. The sensing package 103 may also contain additional components such as a processor, a power supply, other types of sensors, actuators, and communications interfaces. Sensors may for include for example, without limitation, an accelerometer, a light sensor, a sound sensor, a pressure sensor, a presence sensor, a temperature sensor, a humidity sensor, a pH sensor, a TDS sensor, or a salinity sensor. Communications interfaces may include for example, without limitation, Bluetooth, Bluetooth Low Energy, Wi-Fi, or any other wired or wireless networking technology or protocol. Actuators may include for example, without limitation, lights, displays, speakers, or vibration actuators.

The capacitive sensor strips 104a, 104b, and 104c are enclosed in housing 105, and the entire sensing package 103 is installed along the outside wall of hopper 101. The sensing strips therefore may not make direct contact with the liquid in hopper 101. Moreover, there may be multiple layers of air and wall or housing material between the liquid and the sensor. Although liquid levels in the hopper 101 still affect the measured capacitance of the sensing strips, the signals may be relatively weak or noisy due to the layers between the strips and the liquid. As described below, in one or more embodiments the capacitance signals may be processed to provide reliable flow metrics despite the layers between the sensors and the sensed liquid.

The capacitive sensor strips may be placed in any locations with any amount of spacing between the strips. Spacing between strips need not be uniform. In an illustrative embodiment, the bottom of the first horizontal sensor strip 104a may start at 1 inch from the bottom of the wand 103, and the bottom of the second horizontal sensor strip 104b may start at 2 inches from the bottom of the wand 103 (with 1 inch between these horizontal sensor strips). Sensor positioning and spacing may be selected to optimize sensitivity and coverage of possible liquid levels. For example, if the sensors are too close together, they can interfere with one another. If they are spaced too far apart, the upper sensors may not be triggered if the water level in the hopper does not reach a sufficient level above the sensor. Capacitive sensor strips may be of any shape or size.

Figure 2:
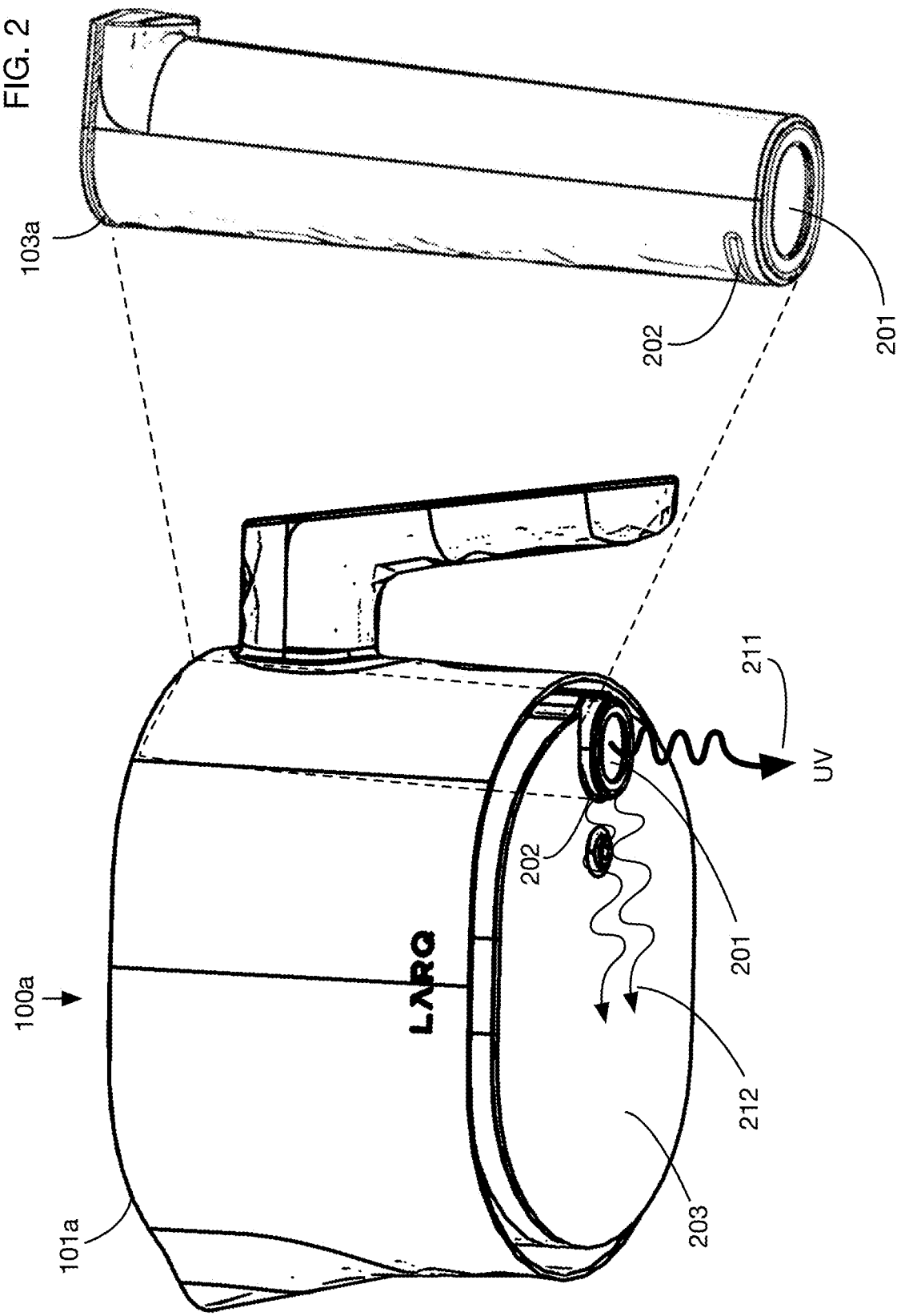
FIG. 2 shows an illustrative embodiment with an ultraviolet light source that may be used for sanitizing the liquid in the container or sanitizing portions of the container.

In one or more embodiments, the filtering container may also include one or more means for sanitizing one or more of the liquid, the filter, the hopper, and the reservoir. For example, one or more embodiments may use ultraviolet (UV) light to sanitize any or all of these items. FIG. 2 shows a hopper 101a of an illustrative embodiment 100a, with a wand 103a installed in the hopper. The wand 103a contains an ultraviolet light source that direct ultraviolet radiation 211 through a window 201 at the bottom of the wand, towards the liquid in the reservoir below the hopper. The UV light source may be activated based for example on data received from the capacitive sensor strips, on data from other sensors, or on commands received from external controllers (such as a user's phone), or in response to user input via switches or buttons on the container or the wand. For example, in one or more embodiments, capacitive sensor data may be processed to determine when the container has been refilled, and when the refilled liquid has passed through the filter into the reservoir; the UV light source may then be activated to sanitize the liquid in the reservoir after it has been filtered. In one or more embodiments, the UV light source may be activated after a certain cumulative amount of liquid has been filtered through the filter, or for example to periodically sanitize the filter itself or the hopper or reservoir or any liquid held in the reservoir. In one or more embodiments, the UV light source may be activated periodically after a certain period of time, independent of the amount of liquid that has been filtered.

One or more embodiments may apply UV light to sanitize any type of vessel, including those without filters. These vessels may or may not have capacitive sensor strips or other sensors to detect when liquid is added to or removed from the vessel. Illustrative examples include water bottles, water dispensers, and medical or laboratory containers of fluids.

In the embodiment shown in FIG. 2, the wand 103a also has a side-facing window 202, through which visible light 212 may be emitted. This light 212 may for example be injected into a clear waveguide 203, causing this waveguide 203 to light up, flash, or change color when light 212 is emitted. This capability may be used for example to provide one or more visible signals to users, to communicate status or activity or to prompt users to perform certain actions.

Figure 3:
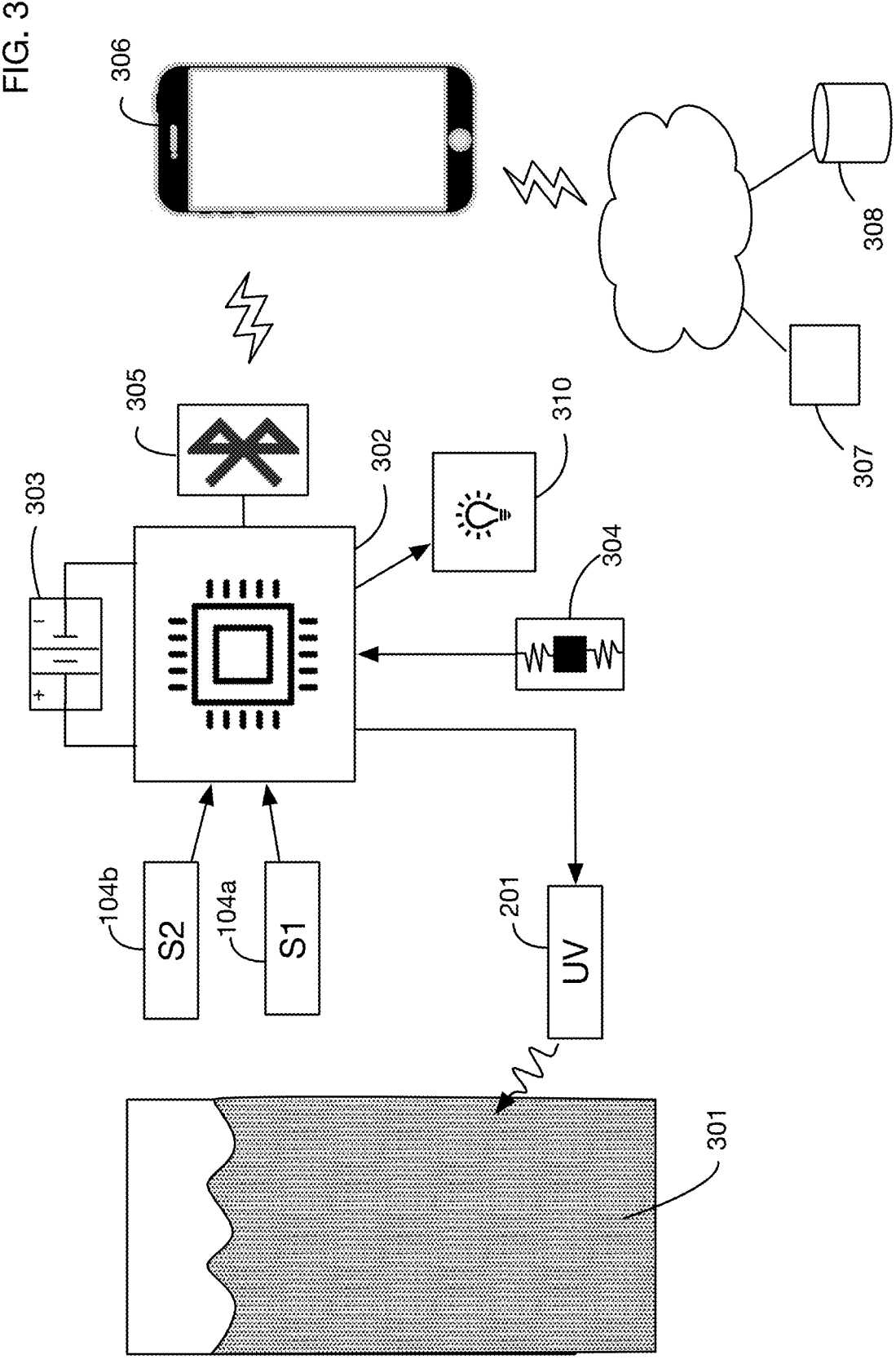
FIG. 3 shows a block diagram of the sensing, processing, and communication components of an embodiment of the invention.

FIG. 3 shows a block diagram of illustrative electronic components in one or more embodiments of the invention. Some or all of these components may be contained in a removable module such as sensing package 103 shown in FIG. 1. In some embodiments, not all of these components may be present. Some embodiments may have additional components beyond those shown in FIG. 3. Illustrative components include capacitive sensors such as sensors 104*a* and 104*b*, which sense changes in the level of liquid 301 in the filtering container; any number of these capacitive sensors may be present. A processor or processors 302 may receive data from these capacitive sensors; the processor 302 may include any auxiliary components or circuits such as signal filters, digital signal processors, and volatile or non-volatile memory. Processor or processors 302 may include for example, without limitation, any type of microprocessor, microcontroller, ASIC, CPU, GPU. An illustrative processor that may be used in one or more embodiments is a Texas Instruments® FDC 1004 processor. A power source 303, such as a battery, a solar power source, or any source of energy, may power processor 302 as well as other components. A port for recharging the power source (or for powering components from an external power source) may also be provided in one or more embodiments. Processor 302 may also be connected to actuators such as UV light source 201, and to other sensors such as an accelerometer 304, a light sensor, a sound sensor, a pressure sensor, a presence sensor, a temperature sensor, a humidity sensor, a pH sensor, a TDS sensor, a salinity sensor, or any other type or types of sensors. Processor 302 may be connected to a communications interface or interfaces 305, which may include for example wireless interfaces that transmit data over Bluetooth or Wi-Fi links. Data may be transmitted for example to or from devices 306 such as a phone, a laptop computer, a tablet computer, a notebook computer, a desktop computer, a server, or any combination or network of these devices. These devices may further process sensor data or other signals. Information may be displayed to user, for example to indicate when a filter should be replaced.

In one or more embodiments, processor 302 may be connected to one or more indicators 310, such as lights, displays, speakers, or vibration actuators, which may be controlled to provide status indications or messages to a user (such as a light while liquid is being filtered, or a flashing light that indicates that a filter should be replaced or inspected). An indicator may explain, respond to, or activate a trigger. Triggers may include for example changes or thresholds related to flow rate, filter life, impurity data, changes or trends or thresholds in data from any sensor associated with the container, comparisons of system data to industry data, latest trends, historical data, calorie count, weight management data, pending notifications. A visual indicator may include a display screen that displays for example graphs, data, text, symbols, graphics, updates, data feeds, goals, comparisons, or competitions. For example, the display may provide a graph or data about flow rate, filter life, impurity data, comparisons of system data to industry data, latest trends, historical data, calorie count, or weight management data. A visual indicator may also include a light (e.g., LED). The light may be a circle, a light bar and/or a light strip that partially or fully extends around the filtering container. The light strip may be located on any part of the container. For example, the light strip may be located near the center of the container and wrap around the entire circumference. The light may turn on/off, change colors, flash, strobe, rotate colors, travel around a path, etc., in response to certain triggers. An audible indicator may include, for example, a recorded voice, synthetic voice, beep, different combinations of beeps or any other sound. A physical indicator may include, for example, a vibration.

In one or more embodiments, data may be transmitted from devices 306 to one or more services 307 or databases 308, for example to record usage information or to order replacement filters automatically when needed. In one or more embodiments, the processor 302 may transmit data to or from services 307 or databases 308 directly, without using an intermediary device 306. Services 307 and databases 308 may for example include websites, apps, social media sites or services (such as FACEBOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, QZONE®, WECHAT®), affiliate or partner websites (such as AMERICAN EXPRESS®, GROUPON®, LIVINGSOCIAL®), other pitchers, Internet-of-Things devices, consumer devices (such as APPLE TV®, MICROSOFT® XBOX®, ROKU®, AMAZON FIRE®, GOOGLE CHROMECAST®, SONY® PLAYSTATION®, NINTENDO® SWITCH®), and central databases. The data may include water quality readings, total dissolved solids (TDS), acidity or PH, or notifications to change the filter. The data may also include parameter extractions from the raw data such as, for example, total volume processed, flow rate, change in flow rate, etc. The data may also include information about optimal filter changes in different regions, during different seasons or during different time frames. The system may automatically determine when the existing filter drops below a certain flow rate, then the system may send a notification via a communication channel (e.g., text, email, website, social media, smart digital assistant, etc.) to facilitate placing an order for a new filter. The system may monitor the number of replacement filters available to a user, then place an order for new replacement filters when the stock of filters is running low.

Services 307 may include one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with the novel pitcher system by also allowing for ordering of new filters, playing music, reading emails, reading texts, making phone calls, question answering, home improvement information, smart home communication/activation, games, shopping, making to-do lists, setting alarms, streaming podcasts, playing audiobooks, and providing weather, traffic, and other real time information, such as news. The ALEXA®, GOOGLE HOME®, and HOMEPOD® systems may also allow the user to access information about eligible transaction accounts linked to an online account across all digital assistant-enabled devices for ordering additional filters or other products/accessories.

Figure 4:
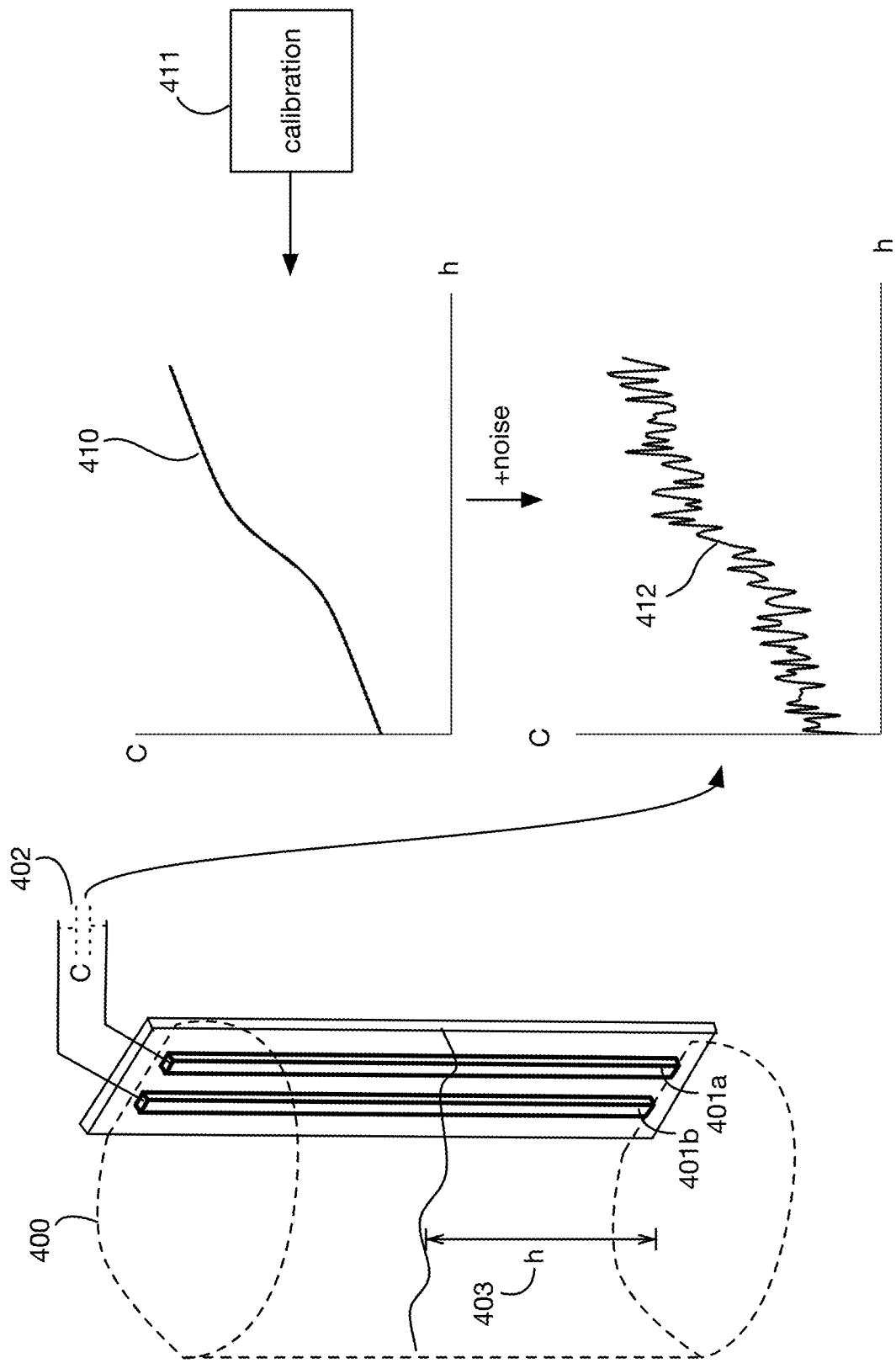
FIG. 4 shows an illustrative flow monitoring device used in the prior art, which uses parallel vertical capacitive strips to monitor the level of a liquid in a container.
Figure 5:
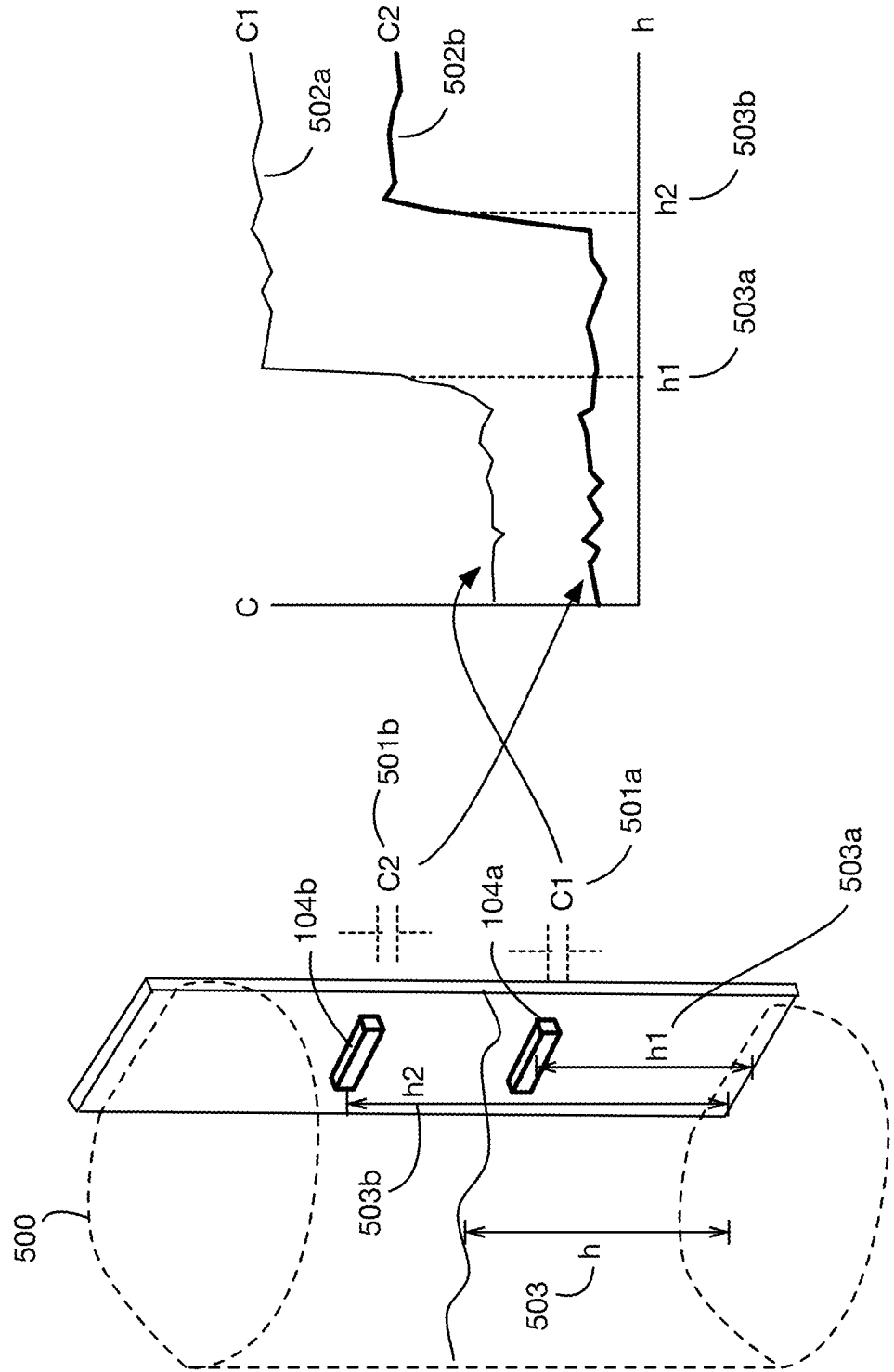
FIG. 5 shows a flow monitoring device used in one or more embodiments of the invention, which uses one or more horizontally oriented capacitive strips to detect when a liquid reaches particular levels; this approach is more robust than the approach illustrated in FIG. 4.

FIGS. 4 and 5 contrast a method used in one or more embodiments of the invention to calculate flow metrics to an approach used in the prior art based on vertical capacitor strips. FIG. 4 shows the vertical strip technique used in the prior art. Two parallel vertical capacitive strips 401*a* and 401*b* may be placed along a wall of a liquid container 400, and the capacitance 402 between these strips may be measured. This capacitance generally changes as the height 403 of the liquid in the container changes; as the liquid level rises, the capacitance also increases. Containers in the prior art that use this technique typically attempt to estimate the height 403 of the liquid continuously (or frequently) from the capacitance signal 402. Flow rates are then calculated from changes in the height 403. This approach presents at least two challenges. First, the relationship 410 between liquid height 403 and capacitance 402 may be a complicated nonlinear curve, due for example to variations in container shape, variable spacing between the vertical strips, or other physical variations. A calibration procedure 411 may therefore be required to determine this curve 410 for each container; recalibration may also be necessary periodically as the physical and electrical characteristics of the container and the strips change over time. Second, the capacitance signal 402 may be influenced significantly by noise; therefore the actual relationship 412 between capacitance and liquid height at any point in time may deviate significantly from the calibration curve 410. As a result, estimates of liquid height from capacitance may have significant errors or uncertainties.

FIG. 5 shows an approach to measuring flow metrics employed in one or more embodiments of the invention. Instead of vertical strips such as strips 401a and 401b of FIG. 4, the illustrative container 500 has one or more horizontal capacitive strips such as strips 104a and 104b. These strips may be of any shape and size, and there may be any number of these horizontal strips. A key difference between the approach shown in FIG. 5 and that of FIG. 4 is that the capacitive strips in FIG. 5 do not extend vertically along the entire container 500 (or along the entire portion of this container for which it is desired to measure liquid flow, such as the hopper portion 101 of the container 100 of FIG. 1). In one or more embodiments the strips 104a and 104b may extend horizontally along a wall of the container 500, and their horizontal dimension may be greater than their vertical dimension; this may not be the case in some embodiments, however. Another difference between the approach illustrated in FIG. 4 and that shown in FIG. 5 is that in one or more embodiments of the invention, the self-capacitance of each sensor strip may be measured to detect liquid changes, as opposed to the mutual capacitance 402 measured in FIG. 4 between the two vertical strips 401a and 401b. This use of self-capacitance may simplify wiring, for example, since only a single conductor may be needed for each horizontal capacitive strip. This self-capacitance may be measured with respect to any convenient ground level; for example self-capacitance 501a may be measured for strip 104a, and self-capacitance 501b may be measured for strip 104b.

Because the horizontal capacitive strips 104a and 104b do not extend vertically along the container 500, the corresponding capacitances 501a and 501b do not vary linearly with the height 503 of the liquid in container 500. Instead, these capacitances change rapidly as the liquid level 503 passes by the corresponding height of each strip. Illustrative curves 502a and 502b show the changes in capacitance 501a and 501b, respectively, as a function of liquid height 503. The zones of rapid change in capacitance correspond to the heights 503a and 503b of the sensors 104a and 104b, respectively. The magnitude of the capacitance change is generally dependent on the surface area of the horizontal strip, which (for a rectangular strip) is the product of the vertical width of the strip and its horizontal length. A narrower strip (with a smaller vertical width) provides a sharper time transition because the liquid level passes from one edge of the strip to the other in less time. However, if the total surface area of the strip is small, the change in capacitance as the liquid passes from one edge of the strip to the other may be relatively small, may make it more difficult to locate the transition. By increasing the horizontal length of the strip, the capacitance can be increased to compensate for a smaller vertical width. Therefore one or more embodiments may use capacitive sensor strips with horizontal lengths that exceed their vertical widths, in order to achieve sharper transitions without reducing total capacitance.

The relative heights of the capacitance curves 502a and 502b are illustrative; in one or more embodiments the upper capacitive strip 104b may have either a higher capacitance or a lower capacitance than the lower capacitive strip 104a. Relative capacitances may depend for example on the local environment of the sensors, such as the distance from the sensor strips to conductive or insulating surfaces, the presence and volume of water in the post-filter reservoir, or the presence or detailed composition of the filtering media. The relative levels between the two capacitive strips are not used; instead only the transition regions for each capacitance curve are used to identify when the liquid level passes the level of each capacitive strip.

Although the capacitance signals 502a and 502b may be noisy, like the capacitance 412 of the vertical strips of FIG. 4, the transitions as the liquid height passes heights 503a and 503b are distinct and can be detected easily despite the noise. One or more embodiments of the invention may therefore use these transition points to calculate flow metrics for the flow of liquid in container 500. This approach may be more robust and effective than the approach described with respect to FIG. 4. In a sense the "analog" measurement of liquid height in the embodiment shown in FIG. 4 is replaced with a "digital" approach in one or more embodiments of the invention, with a resulting improvement in reliability and robustness. As an additional benefit, it may not be necessary to calibrate the capacitance curves 502a and 502b, since detection of the transition points 503a and 503b is possible without knowing the calibration of the entire curves; the absolute values of the capacitance are not used directly so calibration is not required. Also, detection of transition points and processing of the resulting "digital" data may be simpler than the continuous processing of capacitance data in a vertical sensor strip configuration like that described with respect to FIG. 4; the processor complexity and power consumption of this approach may therefore be lower, resulting in lower cost filtering containers.

Figure 6:
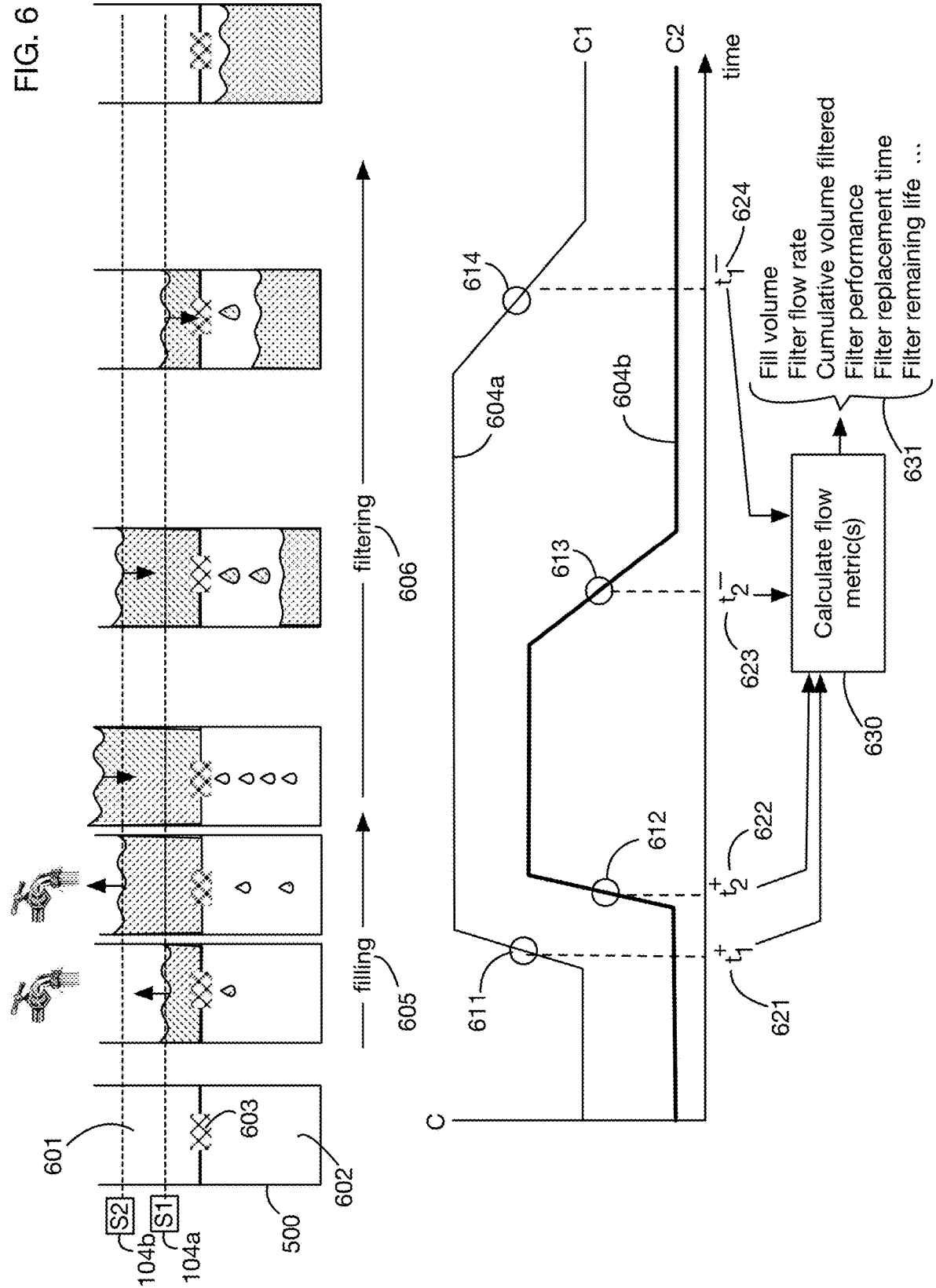
FIG. 6 shows illustrative graphs of capacitance measured by the sensors shown in FIG. 5 as a liquid is filled into the hopper of a container and then filtered into the container's reservoir, and illustrative calculation of flow metrics from points in time on the capacitance curves.

FIG. 6 shows capacitance curves over time 604a and 604b, for capacitances measured by horizontal capacitive strips 104a and 104b, respectively, as a liquid is filled into hopper 601 of filtering container 500, and then passes through filter 603 into reservoir 602 of the container. Filter 603 may be any type of assembly that may remove impurities or otherwise process a liquid; for example, in one or more embodiments it may include filter media as well as a flow restrictor. There is an initial filling phase 605, followed by a filtering phase 606. (A small amount of filtering may occur during the filling phase as well, and may need to be corrected for.) Analysis of the curves 604a and 604b may identify specific points in time that correspond to specific events in the filling and filtering phases; these points in time may then be used in calculation 630 of one or more flow metrics. Illustrative calculations are described below with respect to FIGS. 8 through 12.

FIG. 6 shows illustrative points in time 621, 622, 623, and 624 in capacitance curves 604a and 604b, which may be input into flow metric calculations 630. These points in time may for example correspond to times when the liquid levels in hopper 601 transition past the corresponding heights of sensors 104a and 104b. Time 621 corresponds to event 611 when capacitance 604a is increasing. This time may be anywhere on or near the rising edge of the corresponding capacitance curve, not necessarily in the midpoint of this rising edge. Similarly, time 622 corresponds to event 612 when capacitance 604b is increasing; this time 622 may be anywhere on or near the rising edge of the capacitance curve 604b. Time 623 corresponds to event 613 when capacitance 604b is decreasing, and time 624 corresponds to event 614 when capacitance 604a is decreasing; these times may be anywhere on or near the falling edges of the corresponding capacitance curves. As described below, the time intervals between these identified points in time may be used in calculations 630 to calculate flow metrics that indicate for example the rate at which liquid flows through the filter 603, the total volume of liquid added to the hopper 601, or the rate at which the hopper is filled. Any desired metrics may be calculated from this data, or from trends in this data over time; these metrics may include for example, without limitation, the fill volume (total volume added to the hopper), the fill rate at which liquid is added to the hopper, the filter flow rate, the cumulative volume filtered through the filter over a time period, measures of filter performance, filter replacement times or indicators, and estimates of filter remaining life.

Figure 7:
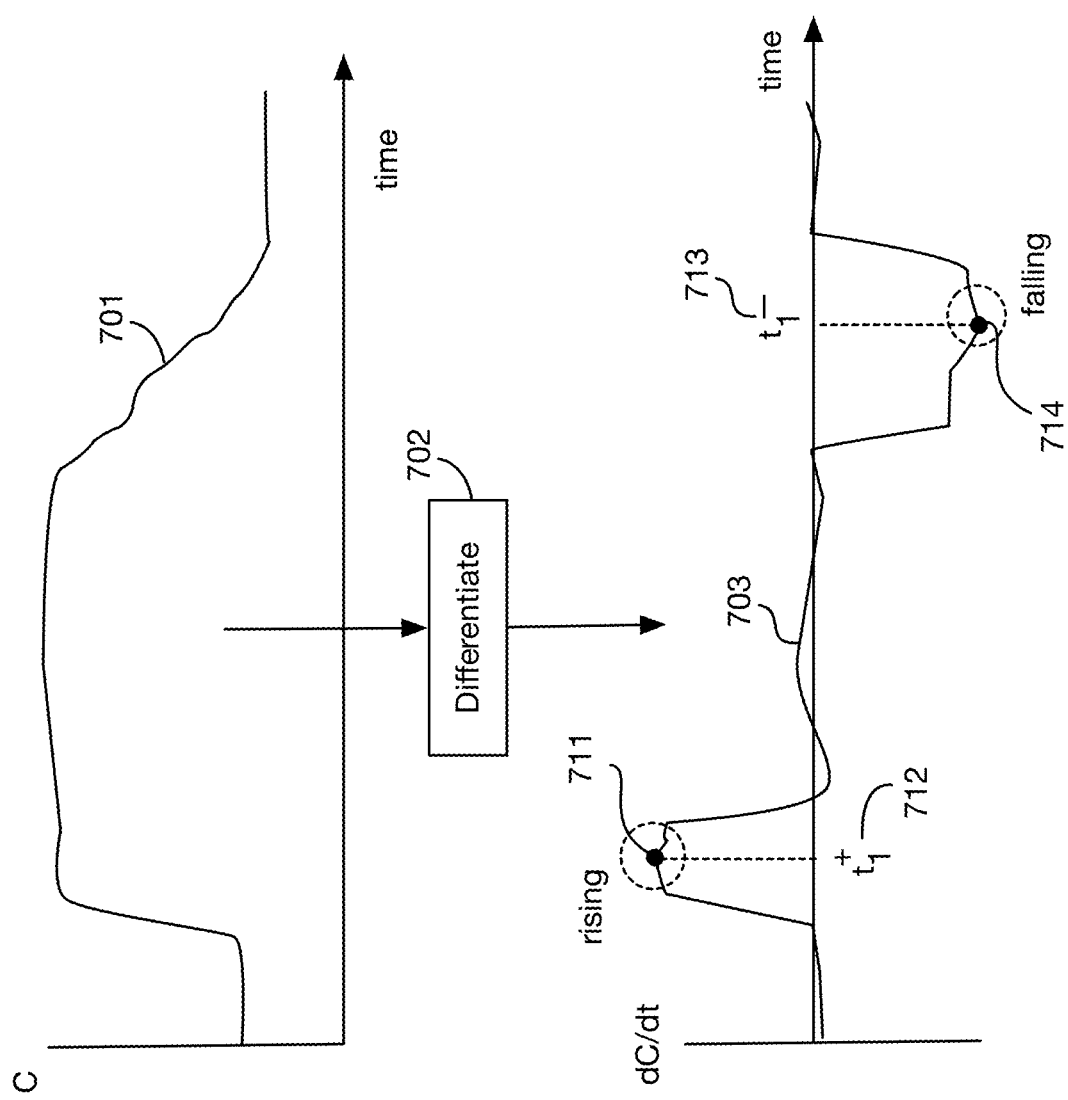
FIG. 7 shows identification of points in time of interest in the capacitance curves by looking for peaks in the curves' derivatives.

FIG. 7 shows an illustrative technique that may be used in one or more embodiments to identify some or all of the points in time that may be used to calculate flow metrics. Illustrative capacitance curve 701 shows the capacitance over time for an illustrative horizontal capacitive strip. To find points on the leading and trailing edge of this curve, one or more embodiments may apply a differentiation operation 702 to the curve 701 to obtain a capacitance derivative curve 703. A maximum point 711 on this derivative curve 703 may be located to find a time 712 on the rising edge of the capacitance curve (during filling of the hopper), and a minimum point 713 may be located to find a time 714 on the falling edge of the capacitance curve (during filtering). In one or more embodiments, smoothing or other filtering operations may be applied before or after differentiation 702. The calculation of derivatives may be accomplished using software and/or hardware. Use of derivatives helps to eliminate DC offsets and highlights transitions (e.g., fill points and when the water level crosses a sensor strip). DC offsets may include, for example, the wearing down of the electrodes, electrical noise that impacts the system, metal objects such as appliances near the electrodes, etc. For example, while a maximum capacitance level may have been 15 pF in the past, these offsets may cause the maximum capacitance level on the same system to drift to only 12 pF. A system relying on absolute measurement would then need to somehow correct for this. However, embodiments of the invention may be insensitive to this drift since they may look only for changes in amplitude (e.g., a sudden rise in capacitance during filling, followed by a less sudden fall in capacitance during filtering).

Figure 8:
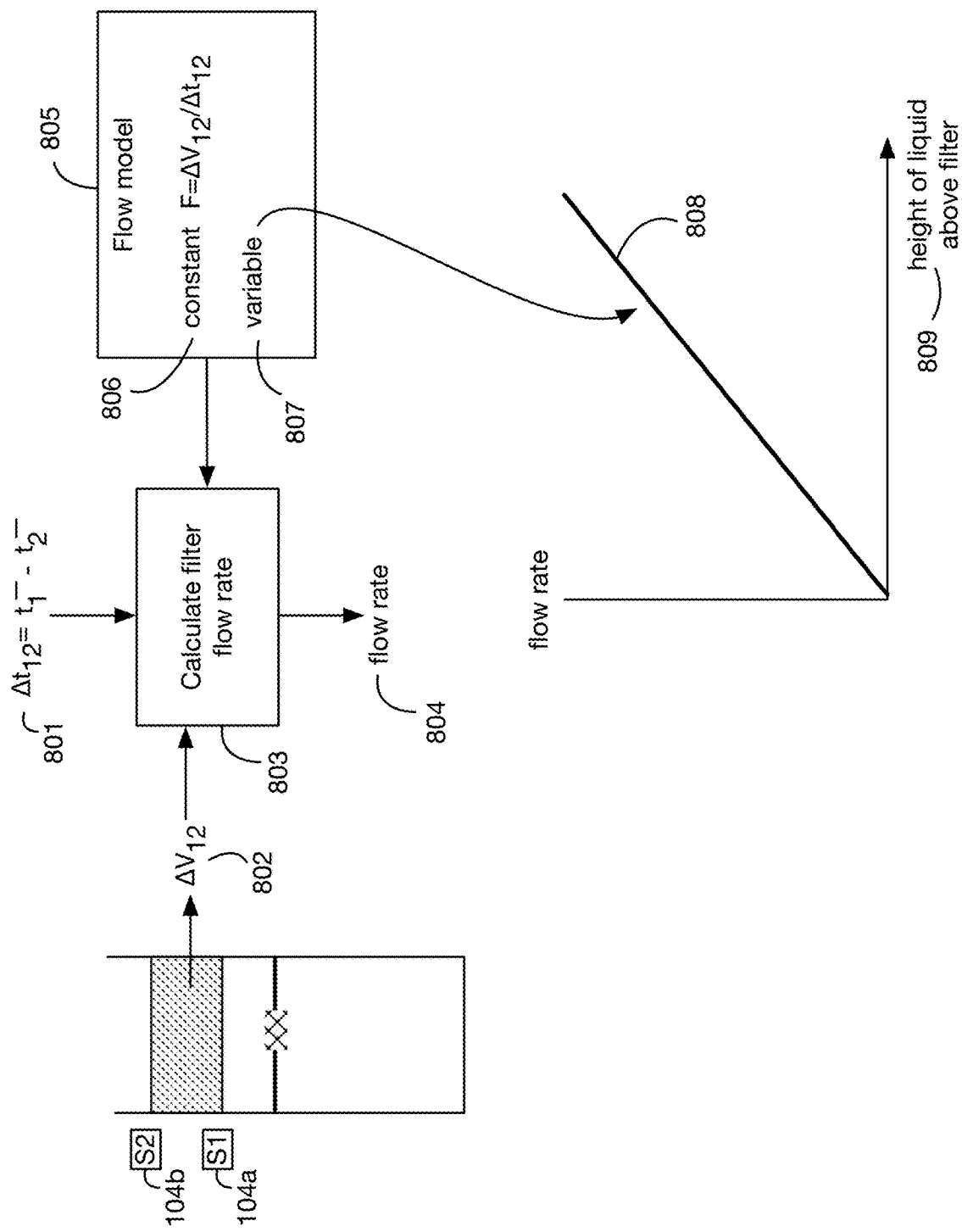
FIG. 8 shows calculation of filter flow rate, an illustrative flow metric, based on the volume of liquid between two horizontal sensor strips and on the points in time that the liquid level passes the position of each of the two strips as it is filtered.

FIG. 8 shows illustrative calculation of a flow rate through the filter from the time difference 801 between the falling edge timepoints of two horizontal capacitive strips 104a and 104b. Since the falling edge time associated with a sensor corresponds at least approximately to the time the liquid height in the hopper transitions past the corresponding height of the sensor, a fixed volume 802 of liquid flows through the filter between the time the liquid reaches the height of the upper sensor 104b and the time it reaches the lower sensor 104a. Using this volume difference 802 and the time 801 required to filter this volume, a calculation 803 can determine the flow rate 804 through the filter. In one or more embodiments, this calculation 803 may be based on a flow model 805 that describes factors that affect the flow rate. A simple constant flow model 806 may for example treat the flow rate through the filter as constant over a short period of time; in this case the flow rate may be calculated as the volume change 802 divided by the time 801. One or more embodiments may use or calculate more complex models 807 with variable flow rates that vary for example as the height of the liquid above the filter changes. For example, one or more embodiments may use a flow rate model where the flow rate 808 through the filter varies linearly with the height 809 of the liquid above the filter. A variable flow rate model may for example assume that the pressure of the liquid on the filter varies with the weight of the liquid, which varies linearly with the height if the hopper has a constant cross sectional area. One or more embodiments may use or derive other variable flow rate models with nonlinear relationships between height and flow rate, or models where the flow rate varies based on additional factors such as temperature, atmospheric pressure, or liquid composition.

Via a calculation similar to 806, which estimates the flow rate through the filter by dividing the known volume 802 between the two sensor strips by the time difference 801 between the falling edges of the capacitance curves, one or more embodiments may calculate the rate at which the hopper is filled by dividing the volume 802 by the time difference between the leading edges of the capacitance curves (612 less 611).

Figure 9:
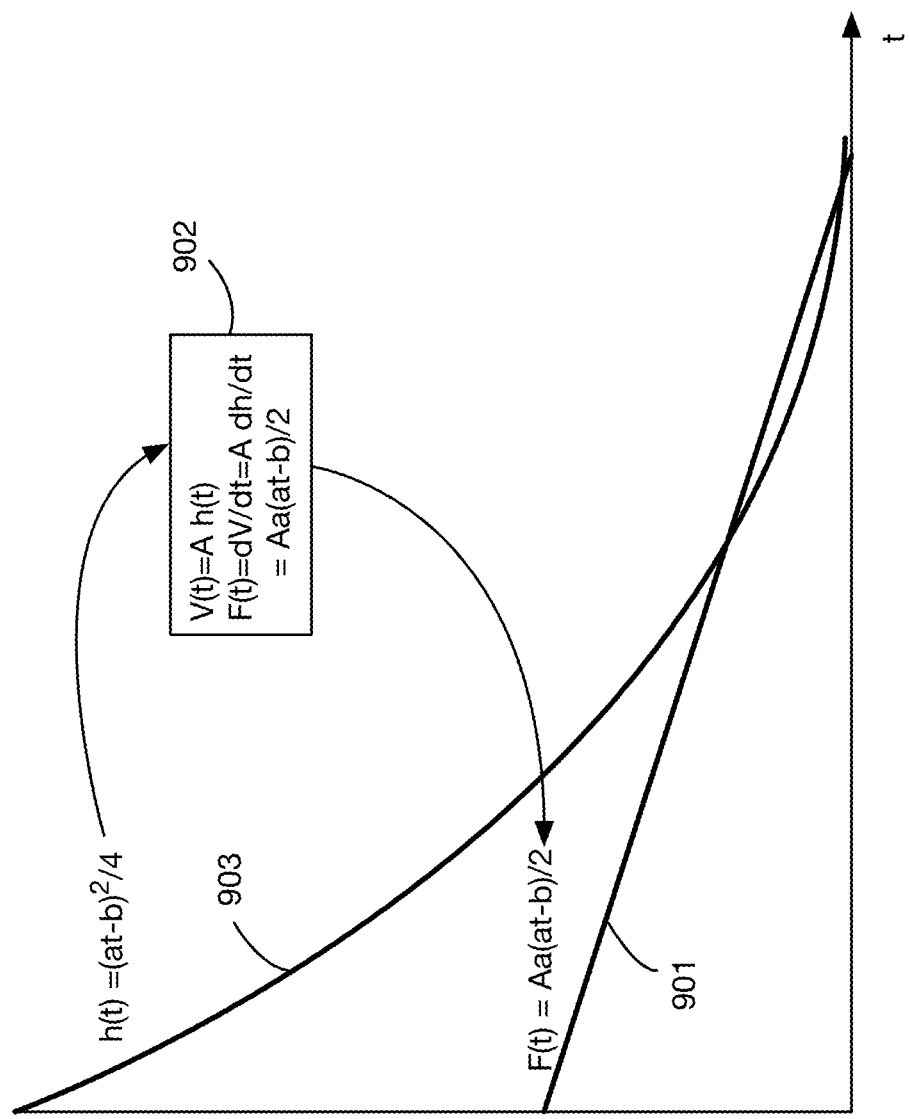
FIG. 9 shows an illustrative flow rate model that may be used in one or more embodiments to calculate flow metrics; in this model, flow rate increases as the height of the liquid in the container increases, due for example to higher pressure of the liquid on the filter.

FIG. 9 shows an illustrative flow rate model that may be used in one or more embodiments of the invention. The inventors have observed that empirically, in many filtering containers, after a hopper is filled with liquid, the flow rate 901 declines over time in an approximately linear relationship as the liquid in the hopper drains through the filter, and the height of the liquid 903 declines on a quadratic curve 903. For a container with constant cross-sectional area A, the flow rate 901 and height 903 will be related via equations 902, since the flow rate is the derivative of the volume in the hopper, and the volume is the cross-sectional area times the height. The quadratic height curve 903 may be parameterized for example by two parameters, a and b, which can be calculated from the capacitive sensor data, as described below.

FIG. 10 shows an example of calculation of the total volume of liquid added to the hopper (the "fill volume") using the flow rate model of FIG. 9. Because the hopper may not always be filled to the same height, the fill volume may be calculated in one or more embodiments from points in time on the capacitance curves. If the hopper is filled relatively quickly (compared to the time required to filter the hopper), the start of the filtering of liquid in the hopper may correspond closely to the time 622 when the liquid level passes the upper sensor 104b. (In other situations, corrections may be applied to compensate for filtering that may occur during filling.) The liquid reaches height 503b corresponding to the upper sensor 104b after a time period 1003b, and it reaches height 503a corresponding to the lower sensor 104a after a time period 1003a. Using the relationship 903 between liquid height and time, these two points 1004a and 1004b on curve 903 may be used to calculate parameters 1005, because they provide two equations in the two unknowns. The total fill height 1001 can then be calculated from these parameters, as well as the total fill volume 1006, and the average flow rate 1007.

Figure 11:
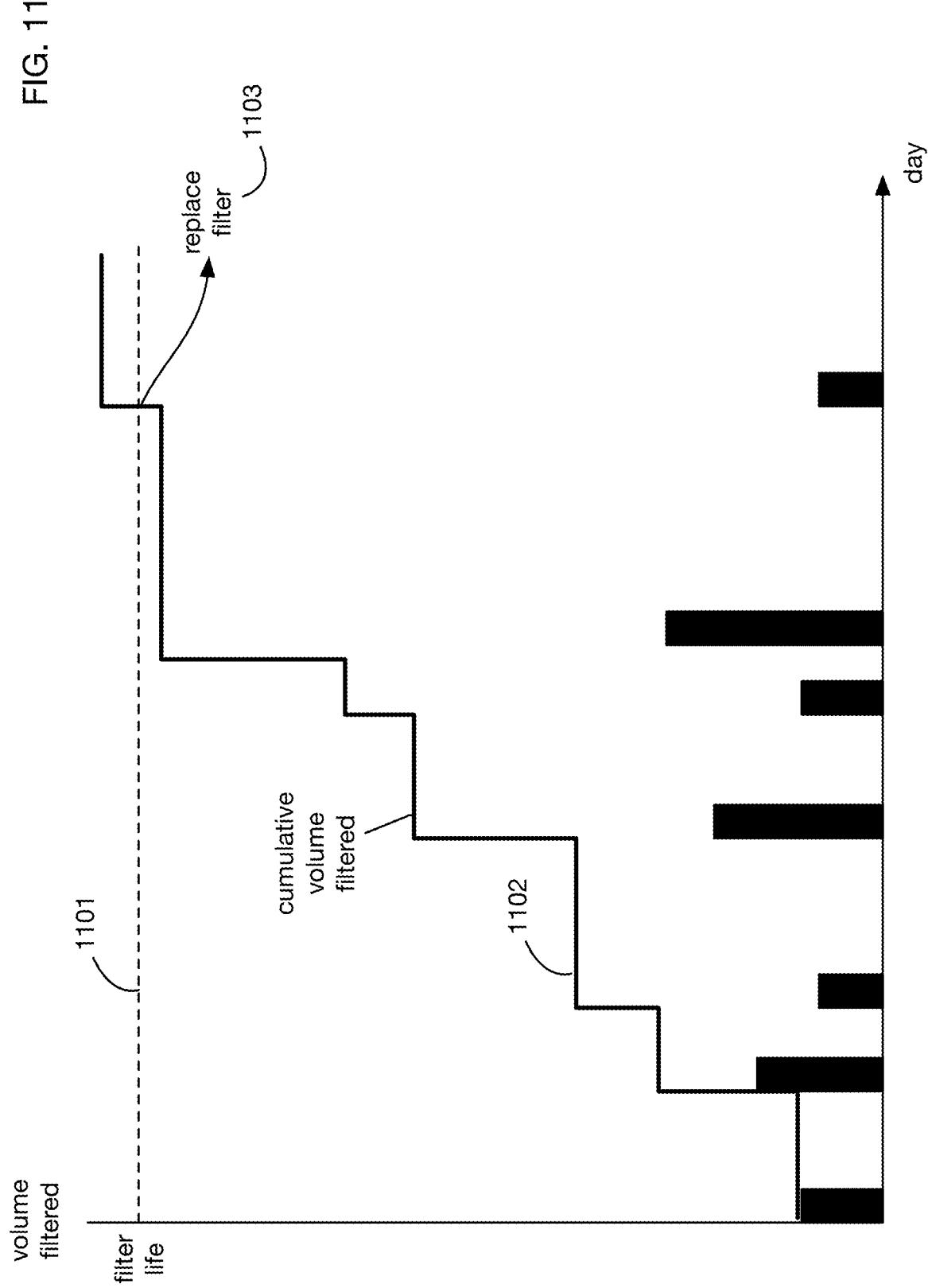
FIG. 11 illustrates calculation of the cumulative volume of liquid that passes through a filter, and use of this cumulative volume to signal when a filter should be replaced.

FIG. 11 shows how tracking of the fill volume into the hopper over a period of time may be used to determine when a filter needs to be replaced. Typically a filter may be rated to filter a specific cumulative amount of volume 1101 over its lifetime before being replaced. One or more embodiments of the invention may track the cumulative volume filtered to date 1102 through a filter by adding the fill volume to the running total each time the hopper is filled. This cumulative volume filtered 1102 may for example be tracked on a user's phone or in an internet database, or within the processor of the sensor package of the filtering container. A user may for example reset the cumulative volume filtered to zero when a new filter is installed, or in one or more embodiments a sensor in the container may detect when a new filter is installed, and may trigger a reset of the cumulative volume. When the cumulative volume filtered 1102 exceeds (or nears) the filter life 1101, a signal or message 1103 may be transmitted indicating that the filter should be replaced.

Figure 12:
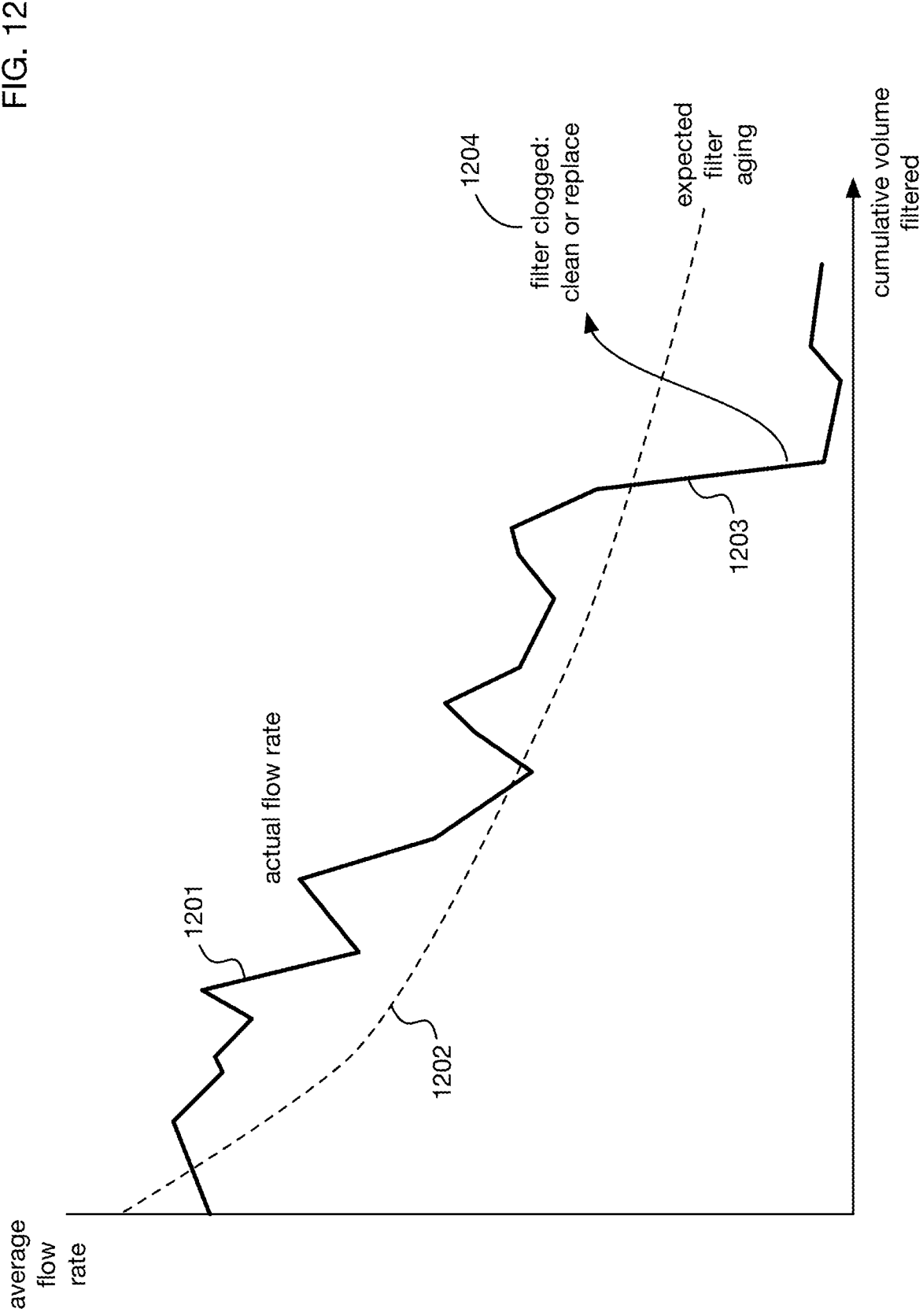
FIG. 12 illustrates tracking of changes in flow rate over time to determine when a filter may be clogged or may need to be replaced.

In addition to tracking cumulative volume filtered, one or more embodiments of the invention may track the filter flow rate over a period of time, as illustrated in FIG. 12. The measured flow rate 1201 may be compared to curve of the expected flow rate as a function of the cumulative volume filtered by a filter. Typically the flow rate will decrease as more volume is filtered through the filter. If this tracking shows a sudden discontinuity 1203 where the actual flow rate falls significantly below the expected value, a signal or message 1204 may be generated to suggest that the filter be cleaned or replaced.

Figure 13:
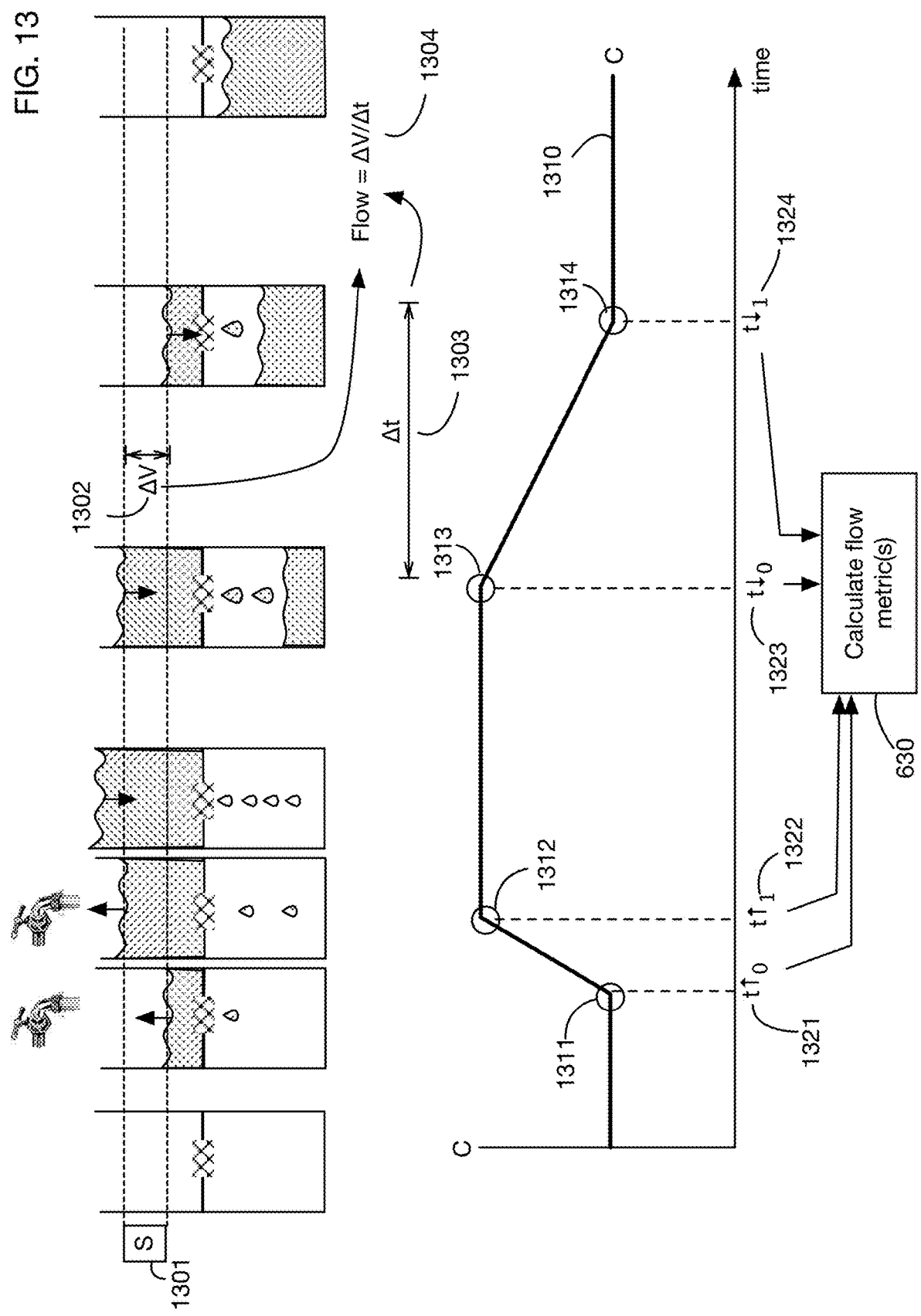
FIG. 13 shows a variation of the two-sensor strip embodiment of FIG. 5, which uses a single horizontal sensor strip and calculates flow metrics from points in time on the capacitance signal from this single strip.

Although the illustrative embodiments described above typically show two horizontal capacitive strips, one or more embodiments may use any number of strips; in particular, one or more embodiments may use only a single capacitive strip and may use the beginning and end points of the rising and falling edges of the capacitance curve as the points in time from which flow metrics are calculated. An embodiment with a single capacitive strip is illustrated in FIG. 13. The points in time 1321, 1322, 1323, and 1324 on the capacitance curve for sensor 1301 correspond respectively to the start of rising capacitance 1311, the end of rising capacitance 1312, the start of falling capacitance 1313, and the end of falling capacitance 1314. These points in time may be used to calculate flow metrics 630, as described above. In particular, an average flow rate 1304 may be calculated from the volume difference 1302 in the hopper between the liquid level at the top of sensor 1301 and the bottom of sensor 1301, and from the time difference 1303 between the time the liquid level passes the top edge of the sensor and the time it passes the bottom edge of the sensor. Similarly, an average hopper fill rate may be calculated from volume difference 1302 and the time difference between 1322 and 1321.

Figure 14:
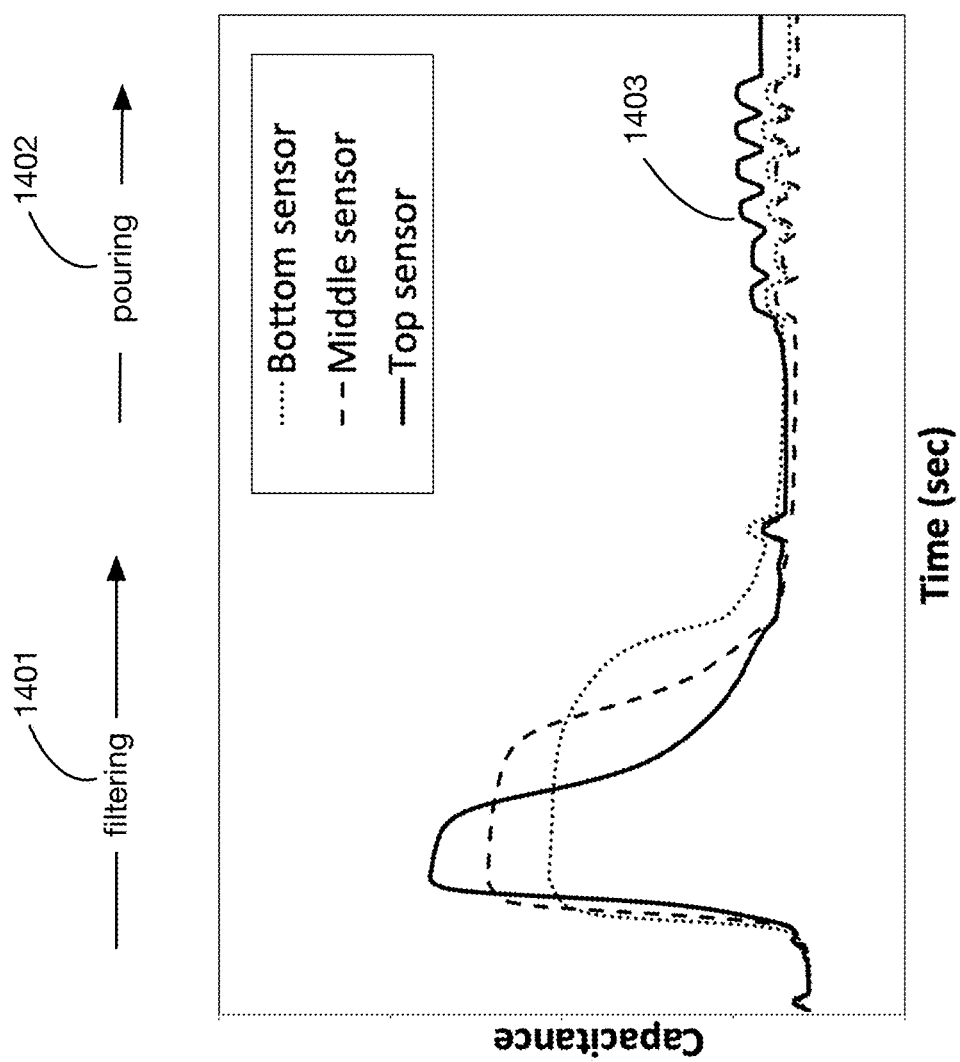
FIG. 14 shows capacitance signals when liquid is poured out of container after filtering, showing that the effect of this pouring is small.

In some situations, liquid in the hopper or reservoir of the filtering container may shift or slosh, due for example to movement of the container. This motion of the liquid may affect the capacitance of the capacitive sensor strips. One or more embodiments may process the capacitance signals, or combine capacitance data with other sensor data, to ensure that flow and filling metrics can be calculated even if the liquid in the container is in motion. Experiments by the inventors have shown that motion of the container when the liquid is in the reservoir, for example tilting the container to pour liquid out of it, has only a minor effect on measured capacitance if the sensors are not located near the reservoir's pour spout. (For this reason, in one or more embodiments the sensing package or "wand" containing the capacitive sensor strips may be physically located away from the pour spout.) FIG. 14 shows an illustrative experiment with three horizontal capacitive strips in a sensing package installed next to the hopper; liquid is added to a hopper and filtered in step 1401 into the reservoir, and then is poured in step 1402 out of the container. During pouring, the effect 1403 on capacitance signals is small, so that these capacitance changes can be easily differentiated from filling the hopper and filtering liquid through the filter. Alternately the different shapes of the capacitance vs time curves can be used to distinguish water filtering from pouring from the reservoir. In one or more embodiments, the system may have additional sensors (such as motion sensors or tilt sensors) that may be used to indicate when pouring is occurring, so that it can be distinguished from filtering.

Figure 15:
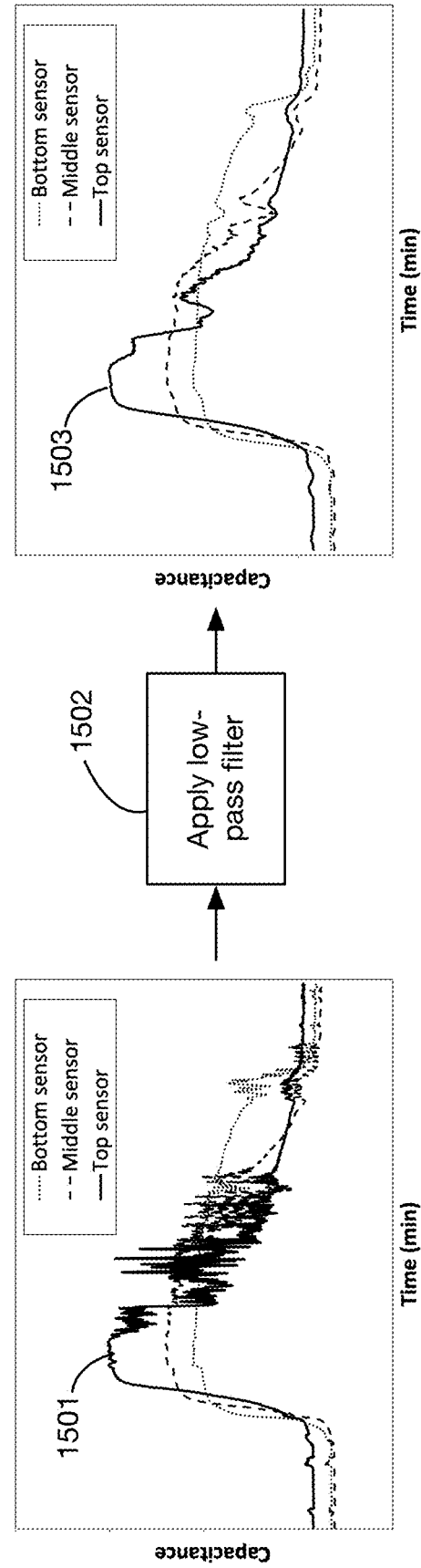
FIG. 15 illustrates filtering of the capacitance data from sensor strips to remove the effect of motion on the data when the container is moved during filtering.

Movement of the filtering container during filtering presents a more significant challenge, as illustrated for example in FIG. 15. In this experiment, a user held a container and walked with the container while liquid was filtered from the hopper. The resulting capacitance signals 1501 show significant noise due to the movement of the container. To compensate for this noise, one or more embodiments may for example apply a low-pass filter 1502 to the capacitance signals; this procedure is effective since the motion component of the signals are generally much higher frequency than the changes due to the fluid level rising and falling due to filling and filtering. The resulting filtered signals 1503 show the rising and falling edges clearly, allowing for calculation of flow metrics as described above. In various embodiments, the system may use software, numerical and/or hardware filtering.

Instead of or in addition to filtering the capacitance data, one or more embodiments may incorporate a baffle in the hopper to reduce movement of the liquid during filtering. The baffle may be for example a flexible (e.g., plastic) barrier to absorb energy and dampen the sloshing.

Figure 16B:
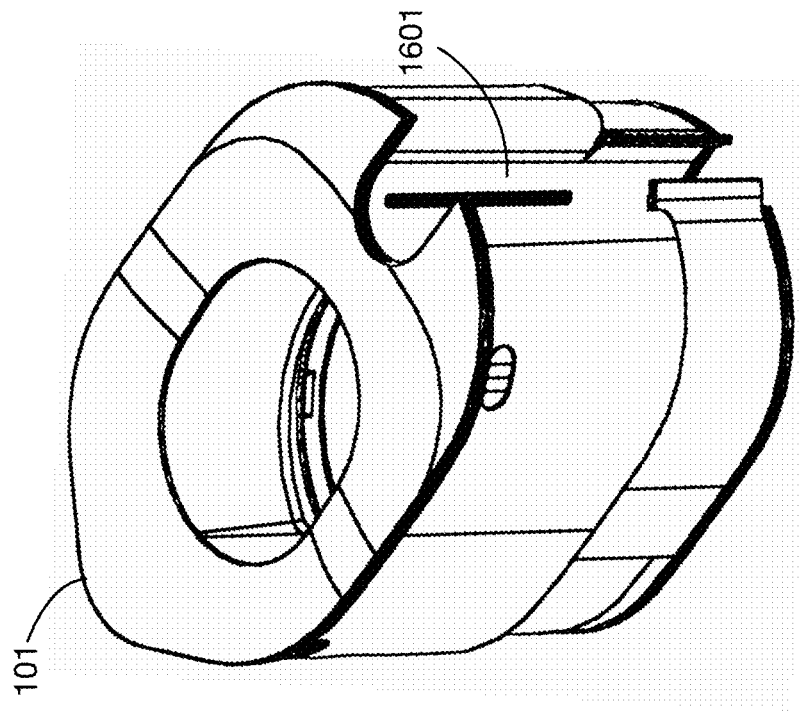
FIGS. 16A and 16B show top and perspective views, respectively, of an embodiment of a hopper with an indentation into which a sensing packaging can be inserted or removed for example for cleaning of the container.
Figure 16A:
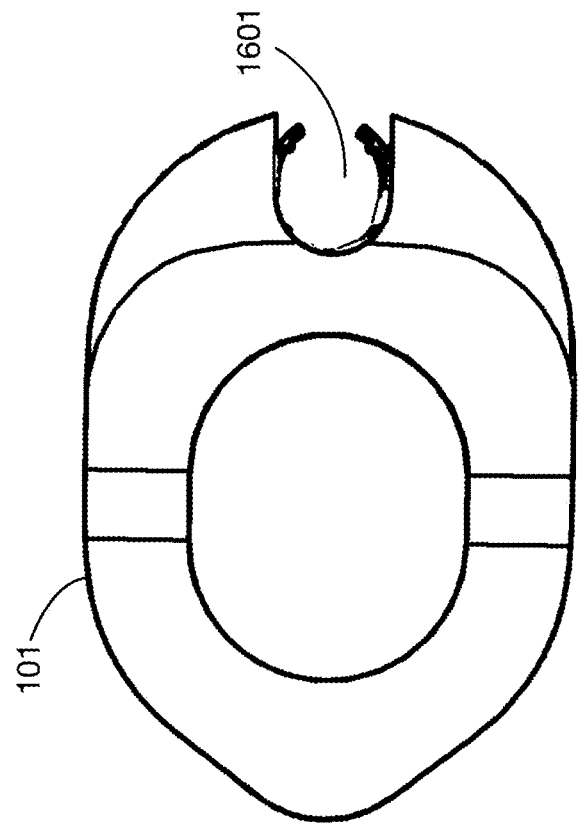

In one or more embodiments, the entire sensing package may be in a removable unit that can attach to the hopper for sensing, and detach from the hopper for example for cleaning of the container. FIGS. 16A and 16B show top and perspective views, respectively, of hopper 101 with the sensing package ("wand") 103 removed. (The handle of the hopper is also not shown for clarity). The walls of hopper 101 have an indentation 1601 into which the wand slides, and from which the wand can be easily removed. The indentation is on the side of the hopper opposite the pour spout, which may reduce the effect of pouring on the capacitance, as described above. This geometry for the hopper and wand is illustrative; one or more embodiments may attach a sensing package to any part of a hopper or other part of a container in any desired manner, using any desired shape and size for the hopper, container, and sensing package.

While the invention herein disclosed has been described by means of specific embodiments and applications thereof, numerous modifications and variations could be made thereto by those skilled in the art without departing from the scope of the invention set forth in the claims.

What is claimed is:

1. A filtering container with time-based capacitive flow monitoring, comprising:
   a hopper configured to receive a liquid, said hopper comprising
      an inside wall in contact with said liquid; and an outside wall not in contact with said liquid;
a filter coupled to said hopper and configured to remove one or more substances from said liquid to yield a filtered liquid;
a reservoir positioned in a vertical direction below said hopper, coupled to said filter and configured to receive and store said filtered liquid;
one or more horizontal capacitive sensor strips detachably coupled to said outside wall of said hopper and not in contact with said liquid and not in contact with said inside wall of said hopper, wherein
said one or more horizontal capacitive sensor strips do not extend vertically across a full height of said liquid in said hopper when said hopper is filled with said liquid, and each horizontal capacitive sensor strip of said one or more capacitive sensor strips comprises a horizontal strip length in a horizontal direction and a vertical strip width in a vertical direction, wherein said horizontal strip length is greater than said vertical strip width; and,
a processor configured to
receive capacitance data from each of said one or more horizontal capacitive sensor strips;
identify points in time in said capacitance data from said each of said one or more horizontal capacitive sensor strips, wherein each point in time of said points in time corresponds to an associated height of said liquid in said hopper;
calculate one or more flow metrics from said points in time, wherein said one or more flow metrics comprises flow rate of said liquid.

2. The filtering container with time-based capacitive flow monitoring of claim 1, wherein said capacitance data comprises a self-capacitance of each horizontal capacitive sensor strip of said one or more horizontal capacitive sensor strips.

3. The filtering container with time-based capacitive flow monitoring of claim 1, wherein said processor is further configured to analyze one or more of said capacitance data and said one or more flow metrics over a time period to determine when said filter needs to be replaced.

4. The filtering container with time-based capacitive flow monitoring of claim 1, wherein
a first time of said points in time corresponds to an associated first height of said liquid in said hopper;
a second time of said points in time corresponds to an associated second height of said liquid in said hopper, wherein
said second time is after said first time, and
said second height is below said first height;
said calculate said one or more flow metrics comprises
obtain or calculate a volume difference between
a first amount of said liquid in said hopper having said first height; and,
a second amount of said liquid in said hopper having said second height;
calculate a time difference comprising said second time less said first time; and,
calculate a flow rate through said filter based on said volume difference and on said time difference.

5. The filtering container with time-based capacitive flow monitoring of claim 4, wherein said processor is further configured to analyze changes in said flow rate through said filter over time to determine when said filter is clogged or when said filter needs to be replaced.

6. The filtering container with time-based capacitive flow monitoring of claim 4, wherein said calculate said flow rate through said filter is further based on a flow rate model.

7. The filtering container with time-based capacitive flow monitoring of claim 6, wherein said flow rate model comprises a constant flow rate.

8. The filtering container with time-based capacitive flow monitoring of claim 6, wherein said flow rate model comprises a variable flow rate.

9. The filtering container with time-based capacitive flow monitoring of claim 8, wherein said variable flow rate varies with a height of said liquid.

10. The filtering container with time-based capacitive flow monitoring of claim 4, wherein
said one or more horizontal capacitive sensor strips comprise
a first horizontal capacitive sensor strip at said first height;
a second horizontal capacitive sensor strip at said second height;
said first time comprises a point in time when said capacitance data associated with said first horizontal capacitive sensor strip is decreasing; and,
said second time comprises a point in time when said capacitance data associated with said second horizontal capacitive sensor strip is decreasing.

11. The filtering container with time-based capacitive flow monitoring of claim 4, wherein
said one or more horizontal capacitive sensor strips comprise a single horizontal capacitive sensor strip;
said first time comprises a point in time when said capacitance data associated with said single horizontal capacitive sensor strip begins decreasing;
said second time comprises a point in time when said capacitance data associated with said single horizontal capacitive sensor strip stops decreasing;
said first height comprises a height of a top edge of said single horizontal capacitive sensor strip; and,
said second height comprises a height of a bottom edge of said single horizontal capacitive sensor strip.

12. The filtering container with time-based capacitive flow monitoring of claim 1, wherein
a first time of said points in time corresponds to an associated first height of said liquid in said hopper;
a capacitance of a horizontal capacitive sensor strip of said one or more horizontal capacitive sensor strips at said first height is increasing at said first time;
a second time of said points in time corresponds to said associated first height of said liquid in said hopper, wherein
said second time is after said first time;
said capacitance of said horizontal capacitive sensor at said first height is decreasing at said second time;
said calculate said one or more flow metrics comprises
obtain or calculate a flow rate through said filter;
calculate a time difference comprising said second time less said first time; and,
calculate a liquid volume added to said hopper based on said flow rate through said filter and based on said time difference.

13. The filtering container with time-based capacitive flow monitoring of claim 12, wherein said processor is further configured to analyze a total value of said liquid volume added to said hopper over time to determine when said filter needs to be replaced.

14. The filtering container with time-based capacitive flow monitoring of claim 12, wherein said calculate said liquid volume added to said hopper is further based on a flow rate model.

15. The filtering container with time-based capacitive flow monitoring of claim 14, wherein said flow rate model comprises a constant flow rate.

16. The filtering container with time-based capacitive flow monitoring of claim 14, wherein said flow rate model comprises a variable flow rate.

17. The filtering container with time-based capacitive flow monitoring of claim 16, wherein said variable flow rate varies with a height of said liquid.

18. The filtering container with time-based capacitive flow monitoring of claim 1, further comprising
a sensing package detachably coupled to said outside wall of said hopper, wherein said sensing package comprises a sensing package housing; and,
said one or more horizontal capacitive sensor strips.

19. The filtering container with time-based capacitive flow monitoring of claim 18, wherein said one or more horizontal capacitive sensor strips are inside said sensing package housing.

20. The filtering container with time-based capacitive flow monitoring of claim 18, wherein
said outside wall of said hopper mates with said sensing package housing to hold said sensing package in position when said sensing package is detachably coupled to said outside wall of said hopper.

21. The filtering container with time-based capacitive flow monitoring of claim 1, wherein said processor is further configured to transmit a message or command based on said capacitance data.

22. The filtering container with time-based capacitive flow monitoring of claim 21, further comprising
an ultraviolet light coupled to said processor, said ultraviolet light oriented to direct ultraviolet radiation toward one or more of said hopper, said filter, said reservoir, said liquid, and said filtered liquid;
wherein said command comprises an activation of said ultraviolet light.

23. The filtering container with time-based capacitive flow monitoring of claim 1, further comprising one or more additional sensors coupled to said processor.

24. The filtering container with time-based capacitive flow monitoring of claim 23, wherein said one or more additional sensors comprise a motion sensor.

25. The filtering container with time-based capacitive flow monitoring of claim 24, wherein said processor is further configured to analyze motion data from said motion sensor to determine whether changes in said capacitance data are due to motion of said filtering container.

* * * * *